US011576895B2

(12) United States Patent
Oronsky et al.

(10) Patent No.: US 11,576,895 B2
(45) Date of Patent: Feb. 14, 2023

(54) COMPOSITIONS AND METHODS FOR INTRAVENOUS ADMINISTRATION OF 2-BROMO-1-(3,3-DINITROAZETIDIN-1-YL)-ETHANONE

(71) Applicant: EpicentRx, Inc., La Jolla, CA (US)

(72) Inventors: Bryan T. Oronsky, Los Altos Hills, CA (US); Jan Scicinski, Saratoga, CA (US); Scott Caroen, San Francisco, CA (US)

(73) Assignee: EPICENTRX, INC, La Jolla, CA (US)

( * ) Notice: Subject to any disclaimer, the term of this patent is extended or adjusted under 35 U.S.C. 154(b) by 597 days.

(21) Appl. No.: 16/069,012

(22) PCT Filed: Jan. 11, 2017

(86) PCT No.: PCT/US2017/012948
§ 371 (c)(1),
(2) Date: Jul. 10, 2018

(87) PCT Pub. No.: WO2017/123593
PCT Pub. Date: Jul. 20, 2017

(65) Prior Publication Data
US 2019/0307723 A1    Oct. 10, 2019

Related U.S. Application Data

(60) Provisional application No. 62/277,236, filed on Jan. 11, 2016.

(51) Int. Cl.
| A61K 31/397 | (2006.01) |
| A61P 35/02 | (2006.01) |
| A61P 35/00 | (2006.01) |
| A61K 9/00 | (2006.01) |
| A61K 31/194 | (2006.01) |
| A61K 31/727 | (2006.01) |
| A61K 35/14 | (2015.01) |
| A61K 47/10 | (2017.01) |
| A61K 47/18 | (2017.01) |
| A61K 47/46 | (2006.01) |
| A61K 9/08 | (2006.01) |

(52) U.S. Cl.
CPC .......... A61K 31/397 (2013.01); A61K 9/0019 (2013.01); A61K 31/194 (2013.01); A61K 31/727 (2013.01); A61K 35/14 (2013.01); A61K 47/10 (2013.01); A61K 47/18 (2013.01); A61P 35/00 (2018.01); A61P 35/02 (2018.01); A61K 9/08 (2013.01); A61K 47/46 (2013.01)

(58) Field of Classification Search
CPC .................................................. A61K 31/397
See application file for complete search history.

(56) References Cited

U.S. PATENT DOCUMENTS

| 2,978,453 | A | 4/1961 | Milton |
| 3,845,770 | A | 11/1974 | Theeuwes et al. |
| 3,916,899 | A | 11/1975 | Theeuwes et al. |
| 4,584,130 | A | 4/1986 | Bucci et al. |
| 4,765,539 | A | 8/1988 | Noakes et al. |
| 5,112,598 | A | 5/1992 | Biesalski |
| 5,336,784 | A | 8/1994 | Hiskey et al. |
| 5,521,203 | A | 5/1996 | Adams et al. |
| 5,556,611 | A | 9/1996 | Biesalski |
| 5,579,458 | A | 11/1996 | Yokosuka et al. |
| 5,580,988 | A | 12/1996 | Dave |
| 5,607,830 | A | 3/1997 | Biesel et al. |
| 5,679,777 | A | 10/1997 | Anderson et al. |
| 5,693,794 | A | 12/1997 | Nielsen |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | Van Der Linden et al. |
| 6,133,320 | A | 10/2000 | Yallampalli et al. |
| 6,245,799 | B1 | 6/2001 | Asselin et al. |
| 6,391,911 | B1 | 5/2002 | Bases |
| 6,407,236 | B1 | 6/2002 | Baraldi et al. |
| 7,163,958 | B2 | 1/2007 | Earl et al. |
| 7,507,842 | B2 | 3/2009 | Oehler et al. |
| 7,745,643 | B2 | 6/2010 | Cannizzo et al. |
| 8,178,698 | B2 | 5/2012 | Cannizzo et al. |
| 8,299,053 | B2 * | 10/2012 | Bednarski ............... A61N 5/10 514/210.17 |
| 8,664,247 | B2 | 3/2014 | Scicinski et al. |
| 8,927,527 | B2 * | 1/2015 | Bednarski ............... A61P 9/00 514/150 |
| 9,139,519 | B2 | 9/2015 | Scicinski et al. |
| 9,226,915 | B2 | 1/2016 | Bednarski et al. |

(Continued)

FOREIGN PATENT DOCUMENTS

| DE | 10111049 A1 | 9/2002 |
| EP | 0412211 A1 | 2/1991 |

(Continued)

OTHER PUBLICATIONS

Fareed et al., CAS: 2000:709216, 2000.*
International Search Report and Written Opinion for PCT/US2017/056454 dated Feb. 6, 2018 (12 pages).
International Search Report and Written Opinion for PCT/US2018/041138 dated Oct. 5, 2018 (13 pages).
NCT02489903, May 20, 2019, "RRX-001 in Lung Cancer, Ovarian Cancer and Neuroendocrine Tumors Prior to Re-administration of Platinum Based Doublet Regimens (Quadruple Threat)", https://clinicaltrials.gov/ct2/history/NCT024899037V_1=View#StudyPageTop, 10 pages.

(Continued)

Primary Examiner — Rei Tsang Shiao
(74) Attorney, Agent, or Firm — Morrison & Foerster LLP

(57) ABSTRACT

The invention provides compositions and methods for intravenous administration of 2-bromo-1-(3,3-dinitroazetidin-1-yl)ethanone (ABDNAZ), including formulations containing autologous whole blood and ABDNAZ that can be rapidly administered to a patient by intravenous infusion without any significant pain at the site of infusion.

19 Claims, No Drawings

(56) References Cited

U.S. PATENT DOCUMENTS

| | | |
|---|---|---|
| 9,468,625 B2 | 10/2016 | Scicinski et al. |
| 9,987,270 B1 | 6/2018 | Oronsky et al. |
| 10,149,832 B2 | 12/2018 | Bednarski et al. |
| 10,342,778 B1 | 7/2019 | Oronsky et al. |
| 10,543,208 B2 | 1/2020 | Oronsky et al. |
| 11,008,287 B2 | 5/2021 | Oronsky et al. |
| 11,160,784 B1 | 11/2021 | Oronsky et al. |
| 2002/0137770 A1 | 9/2002 | Nara et al. |
| 2003/0092684 A1 | 5/2003 | Fredekinq et al. |
| 2004/0024057 A1 | 2/2004 | Earl et al. |
| 2004/0167212 A1 | 8/2004 | Bednarski et al. |
| 2005/0070872 A1 | 3/2005 | Sato et al. |
| 2006/0111272 A1 | 5/2006 | Roberts et al. |
| 2006/0211639 A1 | 9/2006 | Bratzler et al. |
| 2007/0135384 A1 | 6/2007 | Bednarski et al. |
| 2008/0255149 A1 | 10/2008 | Dobler et al. |
| 2008/0256149 A1 | 10/2008 | Bansal et al. |
| 2009/0093644 A1 | 4/2009 | Cannizzo et al. |
| 2009/0163466 A1 | 6/2009 | Bednarski et al. |
| 2009/0192085 A1 | 7/2009 | Robson et al. |
| 2010/0247682 A1 | 9/2010 | Gladwin et al. |
| 2010/0260719 A1 | 10/2010 | Zeldis |
| 2011/0130572 A1 | 6/2011 | Cannizzo et al. |
| 2011/0195947 A1 | 8/2011 | Straessler et al. |
| 2012/0149678 A1 | 6/2012 | Oronsky et al. |
| 2013/0053418 A1 | 2/2013 | Scicinski et al. |
| 2013/0123216 A1 | 5/2013 | Bednarski et al. |
| 2014/0220163 A1 | 8/2014 | Babadi et al. |
| 2014/0308260 A1* | 10/2014 | Oronsky ............ A61K 38/1709 424/93.71 |
| 2014/0349988 A1 | 11/2014 | Scicinski et al. |
| 2015/0190465 A1 | 7/2015 | Faivre et al. |
| 2015/0246020 A1 | 9/2015 | Bednarski et al. |
| 2016/0081981 A1 | 3/2016 | Scicinski et al. |
| 2016/0199346 A1 | 7/2016 | Bednarski et al. |
| 2018/0085346 A1 | 3/2018 | Bednarski et al. |
| 2019/0125742 A1 | 5/2019 | Oronsky et al. |
| 2020/0022952 A1 | 1/2020 | Oronsky et al. |
| 2020/0046682 A1 | 2/2020 | Bednarski et al. |
| 2020/0157047 A1 | 5/2020 | Oronsky et al. |
| 2020/0254016 A1 | 8/2020 | Oronsky |
| 2020/0345689 A1 | 11/2020 | Oronsky et al. |
| 2020/0345690 A1 | 11/2020 | Oronsky et al. |
| 2020/0375982 A1 | 12/2020 | Oronsky et al. |
| 2022/0016077 A1 | 1/2022 | Bednarski et al. |
| 2022/0054480 A1 | 2/2022 | Oronsky et al. |

FOREIGN PATENT DOCUMENTS

| | | |
|---|---|---|
| JP | S48-030376 B | 9/1973 |
| JP | S5511509 A | 1/1980 |
| JP | H05155847 A | 6/1993 |
| JP | 2001506974 A | 5/2011 |
| JP | 2014530811 A | 11/2014 |
| WO | WO-1995/032715 A1 | 12/1995 |
| WO | WO-1996/036602 A1 | 11/1996 |
| WO | WO-1998/016485 A1 | 4/1998 |
| WO | WO-1998016502 A1 | 4/1998 |
| WO | WO-1999/016436 A1 | 4/1999 |
| WO | WO-1999/059575 A1 | 11/1999 |
| WO | WO-2000/006143 A1 | 2/2000 |
| WO | WO-2001/077100 A2 | 10/2001 |
| WO | WO-2004/032864 A2 | 4/2004 |
| WO | WO-2004/098538 A2 | 11/2004 |
| WO | WO-2004/113281 A1 | 12/2004 |
| WO | WO-2005/046661 A2 | 5/2005 |
| WO | WO-2006102760 A1 | 10/2006 |
| WO | WO-2007/022121 A2 | 2/2007 |
| WO | WO-2007/022225 A2 | 2/2007 |
| WO | WO-2013/052164 A1 | 4/2013 |
| WO | WO-2013/052803 A2 | 4/2013 |
| WO | WO-2013052164 A1 | 4/2013 |
| WO | WO-2017/123593 A1 | 7/2017 |

OTHER PUBLICATIONS

Drumond, "Transmissible Venereal Tumor treated with Autohemotherapy," Acta Scientiae Veterinariae, vol. 41, 1107, Jan. 23, 2013, pp. 1-4, XP055510134, Retrieved from the Internet: URL:http://www.ufrgs.br/actavet/41/PUB%201107.pdf [retrieved on Sep. 26, 2018].

Oberoi et al., "Nanocarriers for delivery of platinum anticancer drugs," Advanced Drug Delivery Reviews, vol. 65, No. 13, Oct. 8, 2013, pp. 1667-1685, XP028782543.

Zhu et al., "Amino-functionalized nano-vesicles for enhanced anti-cancer efficacy and reduced myelotoxicity of carboplatin," Colloids and Surfaces, B, Biointerfaces, Elsevier, Amsterdam, NL, vol. 157, May 15, 2017, pp. 56-64, XP085152759.

U.S. Appl. No. 11/502,810, Cyclic Nitro Compounds, Pharmaceutical Compositions Thereof and Uses Thereof, Aug. 11, 2006, Patented, U.S. Pat. No. 7,507,842.

U.S. Appl. No. 12/397,651, Cyclic Nitro Compounds, Pharmaceutical Compositions Thereof and Uses Thereof, Mar. 4, 2009, Patented, U.S. Pat. No. 8,299,053.

U.S. Appl. No. 13/655,618, Cyclic Nitro Compounds, Pharmaceutical Compositions Thereof and Uses Thereof, Oct. 19, 2012, Patented, U.S. Pat. No. 8,927,527.

U.S. Appl. No. 14/584,177, Cyclic Nitro Compounds, Pharmaceutical Compositions Thereof and Uses Thereof Dec. 29, 2014 Patented 9,226,915.

U.S. Appl. No. 14/965,062, Cyclic Nitro Compounds, Pharmaceutical Compositions Thereof and Uses Thereof, Dec. 10, 2015, Patented, U.S. Pat. No. 10,149,832.

U.S. Appl. No. 16/353,047, Cyclic Nitro Compounds, Pharmaceutical Compositions Thereof and Uses Thereof, Mar. 14, 2019, Pending.

U.S. Appl. No. 16/284,035, Methods and Compositions Comprising a Nitrite-Reductase Promoter for Treatment of Medical Disorders and Preservation of Blood Products, Feb. 25, 2019, Pending.

U.S. Appl. No. 15/337,378, Treatment of Gliomas Using Organonitro Compound Combination Therapy, Oct. 28, 2016, Patented, U.S. Pat. No. 9,987,270.

U.S. Appl. No. 15/989,862, Treatment of Gliomas Using Organonitro Compound Combination Therapy, May 25, 2018, Published, US 2019-0125742.

U.S. Appl. No. 15/298,735, Treatment of Brain Metastases Using Organonitro Compound Combination Therapy, Oct. 20, 2016, Pending (allowed).

Alderman, D., "A Review of Cellulose Ethers in Hydrophilic Matrices for Oral Controlled-Release Dosage Forms," *Int. J. Pharm. Tech. & Prod. Mfr.*, 1984, vol. 5, No. 3, pp. 1-9.

Ansari et al., "Primary squamous cell carcinoma of the prostate: a rare clinicopathological entity. Report of 2 cases and review of literature," *Urol. Int.*, 2001, vol. 66, No. 4, pp. 216-219 (abstract).

Archibald et al., "Synthesis and X-ray Crystal Structure of 1,3,3-Trinitroazetidine," *J. Org. Chem.*, 1990, vol. 55, pp. 2920-2924.

Bamba et al., "Release Mechanisms in Gelforming Sustained Release Preparations," *Int. J. Pharm.*, 1979, vol. 2, pp. 307-315.

Dave, P., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," *J. Org. Chem.*, 1996, vol. 61, pp. 5453-5455.

During et al., "Controlled Release of Dopamine from a Polymeric Brain Implant: In Vivo Characterization," *Annals of Neurology*, 1989, vol. 25, No. 4, pp. 351-356.

Electrochemical Oxidation of Alkylnitro Compounds PP-1345, A SERDP 'Seed' Activity, initial submission Jun. 30, 2004; amended Aug. 17, 2004; points of contact Scott K. Lusk and Alan N. Green.

Granelli, P. "SEL 1L and Squamous Cell Carcinoma of the Esophagus," *Clinical Cancer Research*, 2004, vol. 10, pp. 5857-5861.

Hiskey et al., "Preparation of 1-Substituted-3,3-Dinitroazetidines," *Journal of Energetic Materials*, 1999, vol. 17, pp. 233-254.

Hockel et al., "Tumor Hypoxia: Definitions and Current Clinical, Biologic, and Molecular Aspects," *Journal of the National Cancer Institute*, 2001, vol. 93, No. 4, pp. 266-276.

(56) References Cited

OTHER PUBLICATIONS

Howard et al., "Intracerebral Drug Delivery in Rats with Lesion-Induced Memory Deficits," *J. Neurosurg.*, 1989, vol. 71, pp. 105-112.
International Search Report for PCT/US2006/031917 dated Jul. 20, 2007.
International Search Report for PCT/US2011/021500 dated May 3, 2011.
Kornblum et al., "Oxidative Substitution of Nitroparaffin Salts," *J. Org. Chem.*, 1983, vol. 48, pp. 332-337.
Langer et al., "Chemical and Physical Structure of Polymers as Carriers for Controlled Release of Bioactive Agents: A Review," *JMS-Rev. Macromol. Chem. Phys.*, 1983, Ch. 23, pp. 61-126.
Langer, R., "New Methods of Drug Delivery," *Science* (1990) vol. 249, No. 4976, pp. 1527-1533.
Levy, R., et al. "Inhibition of Calcification of Bioprosthetic Heart Valves by Local Controlled-Release Diphosphonate," *Science* (1985) vol. 228, No. 4696, pp. 190-192.
Ling et al., "Phase I study of CM-Na combined with concurrent radiochemotherapy for advanced esophageal carcinoma," *Chinese Journal of Cancer*, 2005, vol. 24, No. 5, (abstract).
Lopez-Ferrer et al., "Differences in the O-Glycosylation Patterns Between Lung Squamous Cell Carcinoma and Adenocarcinoma," *Am. J. Clin. Pathol.*, 2002, vol. 118, pp. 749-755.
Maxwell et al., "Hypoxia-inducible factor-1 modulates gene expression in solid tumors and influences both angiogenesis and tumor growth," *Proc. Natl. Acad. Sci. USA*, 1997, vol. 94, pp. 8104-8109.
Sauder, C. "A Preliminary Trial of the Programmable Implantable Medication System for Insulin Delivery," *The New England Journal of Medicine*, 1989, vol. 321, No. 9, pp. 574-579.
Sefton, M., "Implantable Pumps," *CRC Crit. Rev. Biomed. Eng.*, 1987, vol. 14, No. 3, pp. 201-237.
Shokeir, A., "Squamous Cell Carcinoma of the Bladder: pathology, diagnosis and treatment," *BJU International*, 2004, vol. 93, pp. 216-220.
Stratford et al., "Bioreductive drugs into the next millennium," *Anti-Cancer Drug Design*, 1998, vol. 13, pp. 519-528.
Verma et al., "Osmotically Controlled Oral Drug Delivery," *Drug Dev. Ind. Pharm.*, 2000, vol. 26, No. 7, pp. 695-708.
Wilson, et al., "Radiation-activated prodrugs as hypoxia-selective cytotoxins: model studies with nitroarylmethyl quaternary salts," *Anti-Cancer Drug Design*, 1998, vol. 13, pp. 663-685.
Written Opinion of the International Searching Authority for PCT/US2006/031722 dated May 29, 2007.
Written Opinion of the International Searching Authority for PCT/US2006/031917 dated Jul. 20, 2007.
Written Opinion of the International Searching Authority for PCT/US2011/021500 dated May 2011.
Yen et al., "$^{18}$F-FDG Uptake in Squamous Cell Carcinoma of the Cervix is Correlated with Glucose Transporter 1 Expression," *The Journal of Nuclear Medicine*, 2004, vol. 45, No. 1, pp. 22-29.
Raleigh et al. "Pharmacokinetics of Isotretinoin (ISO) in Rats Following Oral Dosing or Aerosol Inhalation," *British J. Cancer*, 1999, vol. 80, Suppl. 2, 96, p. 269.
Australian Examination Report No. 2 on patent application No. 2006279589, dated May 18, 2012.
Dave, P.R. et al., "Convenient Acylative Dealkylation of Tertiary Amines," *Journal of Organic Chemistry*, 2000, vol. 65, pp. 1207-1209.
Feuer et al., "The Mannich reaction of certain dinitro alcohols with glycine and ethanolamine," *Journal of American Chemical Society*, 1954, vol. 76, pp. 5124-5126.
Marchand, A. P. et al., "Additions of X-Y Across the C(3)-N α-Bond in 1-Aza-3-ethylbicyclo[1.1.0]butane, Novel Routes to 3-Substituted Azetidines," *Journal of Organic Chemistry*, 1994, vol. 59, No. 18, pp. 5499-5501.
McKenney et al., "Synthesis and thermal properties of 1,3-dinitro-3-(1', 3'-dinitroazetidin-3'-yl)azetidine (TNDAZ) and its admixtures with 1,3,3-trinitroazetidine (TNAZ)," *Journal of Energetic Materials*, 1998, vol. 16, pp. 199-235.
Oxley J. et al., "Thermal Decomposition Pathways of 1,3,3-Trinitroazetidine (TNAZ), Related 3,3-Dinitroazetidium Salts, and 15N, 13C, and 2H Isotopomers," *Journal of Physical Chemistry* A, 1997, vol. 101, No. 24, pp. 4375-4383.
Padwa et al., "Diastereofacial selectivity in azomethine ylide cycloaddition reactions derived from chiral o-cyanoaminosilanes," *Tetrahedron* (1985) vol. 41, No. 17, pp. 3529-3535.
Peiris, S. M. et al., "Structures of dinitroazetidine and three of its carbonyl derivatives," *Journal of Chemical Crystallography*, 2001, vol. 30, No. 10, pp. 647-653.
Sikder et al., "1,3,3-Trinitroazetidine (TNAZ), a melt-cast explosive: synthesis, characterization and thermal behavior," *Journal of Hazardous Materials*, vol. 113, 2004, pp. 35-43.
Yarmukhamedov et al., "One-step synthesis of substituted 3,5-dinitropiperidines and 1,5-dinitro-3,7-diazabicyclo(3.3.1)nonanes from 1,3-dinitropropanes," *Russian Chemical Bulletin, International Edition*, 2005, vol. 54, No. 2, pp. 414-420.
Crowder et al., (1999) "Vibrational analysis of high-energy compounds: 1,3,3-trinitroazetidine and 1-acetyl-3, 3-dinitroazetidine," *Journal of Energetic Materials*, vol. 17(1), pp. 49-68.
Chawla, Garima, et al., "Challenges in Polymorphism of Pharmaceuticals," CRIPS, vol. 5, No. 1, Jan.-Mar. 2004, pp. 9-12.
Huguenin, Sandra, et al., "Evaluation of the antitumoral potential of different nitric oxide-donating non-steroidal anti-inflammatory drugs (NO-NSAIDs) on human urological tumor cell lines," *Cancer Letters* (2005) vol. 218, pp. 163-170.
Naimi, Ebrahim, et al., "Synthesis of 3'—and 5'-Nitrooxy Pyrimidine Nucleoside Nitrate Esters: "Nitric Oxide Donor" Agents for Evaluation as Anticancer and Antiviral Agents," *J. Med. Chem.* (2003) vol. 46, pp. 995-1004.
Newman, Ann W. and Byrn, Stephen R. "Solid-state analysis of the active pharmaceutical ingredient in drug products," *Drug Discovery Today* (2003) vol. 8, No. 19, pp. 898-905.
Langer, Robert S., et al., eds., "Medical Applications of Controlled Release," vol. 1, Classes of Systems, Ch. 2, pp. 42-67, CRC Press, Inc., Boca Raton, FL, copyright 1984.
Remington, "The Science and Practice of Pharmacy," 19th Edition, vol. II, pp. 1495-1562, 1577-1614, and 1660-1692; Mack Publishing Company, Easton, PA, 1995.
Rosenthal, David I., "A Phase I Single-Dose Trial of Gadolinium Texaphyrin (Gd-Tex), a Tumor Selective Radiation Sensitizer Detectable by Magnetic Resonance Imaging," *Clinical Cancer Research* (1999) vol. 5, No. 4, pp. 739-745.
Smolen, Victor F., et al., eds., "Controlled Drug Bioavailability," vol. 1, Drug Product Design and Performance, Ch. 7, pp. 203-237, John Wiley & Sons, New York, NY, copyright 1984.
Treat, Joseph, et al., "Liposome Encapsulated Doxorubicin: Preliminary Results of Phase I and Phase II Trials," pp. 353-365 of "Liposomes in the Therapy of Infectious Diseases and Cancer, Proceedings of the Ciba-Geigy-Squibb-UCLA Colloquium at Lake Tahoe, CA, Feb. 16-20, 1988," Lopez-Berestein, G. and Fidler, I. J. (eds.), Alan R. Liss, Inc., New York, 1989.
Goodson, J. Max, "Dental Applications," Chapter 6 of Medical Applications of Controlled Release, vol. II, pp. 115-138, CRC Press, Inc., Boca Raton, FL, copyright 1984.
Jia, Q., et al., "NO donors with anticancer activity," *Expert Opin. Therapeut. Patents* (2002) vol. 12, No. 6, pp. 819-826.
Konovalova, N.P., et al., "Nitric oxide donor increases the efficiency of cytostatic therapy and retards the development of drug resistance," *Nitric Oxide* (2003) vol. 8, No. 1, pp. 59-64.
Sandler, G., "Clinical evaluation of propatylnitrate in angina pectoris," *British Medical Journal*, vol. 2, No. 5269 (Dec. 30, 1961), pp. 1741-1744.
Stamler, J.S., et al., "Inhaled ethyl nitrite gas for persistent pulmonary hypertension in infants," *The Lancet* (2002) vol. 360, No. 9350, p. 2077.
International Search Report for PCT/US2006/031722 dated May 29, 2007.
Nitrates and Nitrites Answers to Frequently Asked Questions, Ohio Bureau of Environmental Health, Health Assessment Section, Nov. 1, 2006. (2 pages).

(56) References Cited

OTHER PUBLICATIONS

Johnson, J., et al., "Relationships Between Drug Activity in NCI Preclinical in Vitro and in Vivo Models and Early Clinical Trials," *British J. Cancer* (2001) vol. 84, No. 10, pp. 1424-1431.
Kashfi, Khosrow, et al., "Nitric Oxide-Donating Nonsteroidal Anti-Inflammatory Drugs Inhibit the Growth of Various Cultured Human Cancel Cells: Evidence of a Tissue Type-Independent Effect," *J. Pharmacology Experimental Therapeutics* (2002) vol. 303, No. 3, pp. 1273-1282.
Mendenhall, William M., et al., "Radiation Therapy for Squamous Cell Carcinoma of the Tonsillar Region: A Preferred Alternative to Surgery?" *J. Clinical Oncology* (2000) vol. 18, No. 11, pp. 2219-2225.
Sausville, Edward A., et al., "Contributions of Human Tumor Xenografts to Anticancer Development," *Cancer Research* (2006) vol. 66, No. 7, pp. 3351-3354.
Morales-Suarez-Varela, Maria M., et al., "Impact of Nitrates in Drinking Water on Cancer Mortality in Valencia, Spain," European Journal of Epidemiology, 1995, pp. 15-21, vol. 11.
Prezioso, J.A., et al., Genetic Toxicity Evaluation of 1, 3, 3-Trinitroazetidine, vol. IV: Summary Report on the Genotoxicity of TNAZ, AL/OE-TR-1994-0069 vol. IV of IV, Oct. 1994, 22 pages, Air Force Materiel Command, Wright-Patterson Air Force Base, Ohio.
Simpson, R.L., et al., Characterization of TNAZ, UCRL-ID-119672, Dec. 14, 1994, Lawrence Livermore National Laboratory, 15 pages.
Watt, Duncan S. and Cliff, Matthew D. "Evaluation of 1,3,3-Trinitrozaetidine (TNAZ)—A High Performance Melt-Castable Explosive," Weapons Systems Division, Aeronautical and Maritime Research Laboratory, Melbourne, Australia. Report No. DSTO-TR-1000, Issue date Jul. 2000. (34 pages).
Watt, Duncan S. and Cliff, Matthew D. "TNAZ Based Melt-Cast Explosives: Technology Review and AMRL Research Directions," Weapons Systems Division, Aeronautical and Maritime Research Laboratory, Melbourne, Australia. Report DSTO-TR-0702, Issue date Jul. 1998. (37 pages).
West, Anthony R., Solid State Chemistry and its Applications, 1988, pp. 358, and 365, Wiley, New York.
Akhavan, Jacqueline, Explosives and Propellants, Kirk-Othmer Encyclopedia of Chemical Technology, Sep. 17, 2004, pp. 719-744.
Muehlstaedt et al., Caplus, 1976:89768, Copyright 2008. (1 page).
Crowder et al., caplus an 1999: 171384.
Hiskey et al., caplus an 1993:233785.
Hiskey et al., caplus an 1994:700750.
Zhang et al., caplus an 1998:460439.
International Search Report and Written Opinion for PCT/US2011/064178 dated Apr. 17, 2012. (8 pages).
International Search Report and Written Opinion for PCT/US2012/038592 dated Aug. 10, 2012. (11 pages).
Coburn et al., caplus an 1998:567551.
Garver et al., "Catalyzed Oxidative Nitration of Nitronate Salts," *J. Org. Chem.* 1985, vol. 50, No. 10, pp. 1699-1702.
Hiskey et al., caplus an 1999:411860.
Katritzky et al., "Novel Syntheses of 1,3,3-Trinitroazetidine," *J. Heterocyclic Chem.*, Mar.-Apr. 1994, vol. 31, pp. 271-275.
Marchand et al., "A Novel Approach to the Synthesis of 1,3,3-Trinitroazetidine," *J. Org Chem.* 1995, vol. 60, No. 15, pp. 4943-4946.
Nara et al., caplus an 2002:169585; 2002.
Straessler et al., "Development of a Safe and Efficient Two-Step Synthesis for Preparing 1-Bromoacetyl-3,3-dinitroazetidine, a Novel Clinical Anticancer Candidate," *Organic Process Research & Development*, 2012, vol. 16, pp. 512-517.
Temodar Prescribing Information (year 2008).
"Phase 1 Two Part Dose Escalation Trial of RRx-001 + Radiation + Temozolomide and RRx-001 + Temozolomide Post-RT In Newly Diagnosed Glioblastoma and Anaplastic Gliomas (G-FORCE-1)" from Clinicaltrials.gov, dated Oct. 24, 2016.

"Dose-Escalation Study of RRx-001 in Combination With Whole Brain Radiation in Subjects With Brain Metastases (Brainstorm)" from Clinicaltrials.gov.
Ning, S. et al., "Dinitroazetidines Are a Novel class of Anticancer Agents and Hypoxia-Activated Radiation Sensitizers Developed from Highly Energetic Materials," *Cancer Res.* (2012) vol. 72, pp. 2600-2608.
Oronsky, B. T. et al., "A Review of Two Promising Radiosensitizers in Brain Metastases: Rrx-001 and 2-Deoxyglucose," *J. Cancer Sci. Ther.* (2015) vol. 7, pp. 137-141.
Dave, 1997, caplus an 1997: 67373.
Li et al., 2006, caplus an 2006:150006.
Gladwin et al., "The Emerging Biology of the Nitrite Anion," in Nature Chemistry and Biology, 2005, vol. 1, pp. 308-314, p. 308, col. 1, para 1; p. 308, col. 2, para 2; p. 310, col. 2, para. 3-4; p. 309, figure 1; p. 310, figure 2; p. 311, figure 3.
S.S. Wong in *Chemistry of Protein Conjugation and Cross-linking*; CRC Press: Boca Raton, 1991, p. 147.
Wu et al. in *AAPS PharmSciTech* (2011) vol. 12, pp. 1248-1263.
International Search Report and Written Opinion for PCT/US12/58964, dated Apr. 5, 2013, 9 pages.
Weyerbrock et al., Journal of Neurosurgery, 2003, 99(4), 728-737.
Schwartz, R., Am. J. Health-Syst. Pharm., 2007, 64 (Supplement 2), S5-S13.
Heller, ECS Transactions, 2010, 28(33), 1-6.
Vascular Tumor, 2018, <https://www.cancer.gov/publications/dictionaries/cancer-terms/def/vascular-tumor>.
International Search Report and Written Opinion for PCT/US2017/012948 dated Mar. 28, 2017 (8 pages).
Fitch et al, Abstract WRM 267, "High resolution MS proves that the developmental cancer drug, RRx-001, alkylates the hemoglobin beta chain", 44th Western Regional Meeting of the American Chemical Society, Oct. 3-6, 2013, Available from the Internet, <URL: http://acswrm.org/wrm2013/files/Abstracts_SaturdayAM.pdf>, Last Retrieved Mar. 21, 2017.
Oronsky et al, "RRx-001: a systemically non-toxic M2-to-M1 macrophage stimulating and prosensitizing agent in Phase II clinical trials", Expert Opinion on Investigational Drugs (2017), vol. 26, No. 1, pp. 109-119, Published Dec. 21, 2016.
NCT02489903, Jul. 2, 2015, "An Open-label, Three Stage, Three Arm Pilot Study of RRx-001 For Second Line or Greater Small Cell Lung Cancer, Third Line or Greater Non-Small Lung Cancer, and Second Line or Greater High Grade Neuroendocrine Tumors Prior to Re-administration of Platinum Based Doublet Regimens (Triple Threat)", Available from the Internet, <URL: https://clinicaltrials.gov/archive/NCT02489903/2015_07_02>.
Scicinski et al, "Preclinical Evaluation of the Metabolism and Disposition of RRx-001, a Novel Investigative Anticancer Agent", Drug Metabolism and Disposition (2012), vol. 40, No. 9, pp. 1810-1816.
Cabrales et al, "A look inside the mechanistic black box: Are red blood cells the critical effectors of RRx-001 cytotoxicity?", Medical Oncology (2016), vol. 33, No. 7, Article No. 63, 7 Pages, doi:10.1007/s12032-016-0775-3.
Armstrong et al., (2002). "Role of Glutathione Depletion and Reactive Oxygen Species Generation in Apoptotic Signaling in a Human B Lymphoma Cell Line, Cell Death and Differentiation," Nature, 9:252-263, 2002.
Berge et al., (1997). "Pharmaceutical Salts," Journal of Pharmaceutical Sciences, 66(1):1-19.
Brezezniak et al., (2016). "RRx-001-Induced Tumor Necrosis and Immune Cell Infiltration in an EGFR Mutation-Positive NSCLC with Resistance to EGFR Tyrosine Kinase Inhibitors: A Case Report," Case Rep Oncol., 9:45-50.
Brown et al., (1998). "Tirapazamine: Laboratory Data Relevant to Clinical Activity," Anti-Cancer Drug Design, 13:529-539. Abstract Only.
Carter et al., (2016). "Partial response to carboplatin in an RRx-001 pretreated patient with EGFR-inhibitor-resistance and T790M-negative NSCLC," Respir. Aged Case Rep., 18:62-65.
ClinicalTrials.gov, (2015). "NCT01359982: Safety and Pharmacokinetic Study of RRx-001 in Cancer Subjects (DINAMIC)," available

(56) References Cited

OTHER PUBLICATIONS online at <https://clinicaltrials.gov/ct2/show/NCT02096354?term=RRx-001&draw=1&rank=11>, 7 pages.
ClinicalTrials.gov, (2016). "NCT02096341: A Phase 1 Pilot Study of the Subcutaneous (s.c.) Route to Facilitate the Administration of RRx-001," available online at Khttps://clinicaltrials.gov/ct2/show/NCT02096341 ?term=RRx-001 &draw=1 &rank=3>, 5 pages.
ClinicalTrials.gov, (2018). "NCT03515538: Safety and Efficacy of RRx-001 in the Attenuation of Oral Mucositis in Patients Receiving Chemoradiation for the Treatment of Oral Cancers (Prevlar)," retrieved from the internet <https://clinicaltrials.gov/ct2/show/NCT03515538>, 11 pages.
ClinicalTrials.gov, (2019). "NCT02452970: RRx-001 in Second Line Treatment of Advanced Cholangiocarcinoma Prior to Readministration of First-Line Therapy (EPIC)," available online at <https://clinicaltrials.gov/ct2/show/NCT02452970?term=RRx-001&draw=3&rank=1>, 6 pages.
ClinicalTrials.gov, (2019). "NCT02518958: A Phase I, Open-Label, Multiple Ascending Dose Study of RRx-001 and Nivolumab (Primetime)," available online at <https://clinicaltrials.gov/ct2/show/NCT02518958?term=RRx-001&draw=1&rank=7>, 6 pages.
ClinicalTrials.gov, (2021). "NCT03699956: RRx-001 Sequentially With a Platinum Doublet or a Platinum Doublet in Third-Line or Beyond in Patients With Small Cell Lung Cancer (Replatinum)," available online at <https://clinicaltrials.gov/ct2/show/NCT03699956?term=RRx-001&draw=1 &rank=5>, 8 pages.
ClinicalTrials.gov, (2022). "NCT02096354: A Phase 2 Randomized, Open-Label Study of RRx-001 vs Regorafenib in Subjects With Metastatic Colorectal Cancer (Rocket)," available online at <https://clinicaltrials.gov/ct2/show/NCT02096354?term=RRx-001&draw=1&rank=8>, 8 pages.
ClinicalTrials.gov, (2022). "NCT02801097: RRx-001 in Combination With Irinotecan in Metastatic or Advanced Cancer (Payload) (Payload)," available online at <https://clinicaltrials.gov/ct2/show/NCT02801097?term=RRx-001&draw=1&rank=6>, 6 pages.
ClinicalTrials.gov, (2022). "NCT02871843: RRx-001 + Radiation + Temozolomide In Newly Diagnosed Glioblastoma and Anaplastic Gliomas (G-FORCE-1)," available online at <https://clinicaltrials.gov/ct2/show/NCT02096354?term=RRx-001 &draw=1 &rank=9>, 8 pages.
ClinicalTrials.gov, (2022). "NCT04525014: RRx-001 Given With Irinotecan and Temozolomide for Pediatric Patients With Recurrent or Progressive Malignant Solid and Central Nervous System Tumors (Pirate)," available online at <https://clinicaltrials.gov/ct2/show/NCT02096341 ?term=RRx-001 &draw=1&rank=3>, 10 pages.
Dorman, (2000). "Fulminant babesiosis treated with clindamycin, quinine, and whole-blood exchange transfusion," Transfusion, 40(3):375-80.
European Supplementary Search Report for European Patent Application No. EP12839088.7, published Apr. 28, 2015, 4 pages.
Final Office Action received for U.S. Appl. No. 13/655,618 dated Jun. 12, 2014, 6 pages.
Final Office Action received for U.S. Appl. No. 13/655,618 dated Sep. 11, 2013, 4 pages.
Final Office Action received for U.S. Appl. No. 14/965,062 dated Feb. 6, 2017, 6 pages.
Final Office Action received for U.S. Appl. No. 16/284,035 dated May 26, 2022, 28 pages.
Final Office Action received for U.S. Appl. No. 16/284,035 dated Nov. 15, 2021, 24 pages.
Grisham, (2017). "Pumped Up: Implanted Chemotherapy Device Improves Survival when Colorectal Cancer Spreads to the Liver," available online at <https://www.mskcc.org/news/pumped-implanted-chemotherapy-device-improves-survival-when-colorectal-cancer-spreads-liver>, 5 pages.
Hong et al., (2008). Combining Targeted Therapies, Targeted Cancer Therapy, p. 362, 2 page.
Ignarro, Louis J., Nitric Oxide Biology and Pathology, 2000, pp. 5, 895, and 908, Academic Press.

International Preliminary Report on Patentability dated Jul. 14, 2020 in PCT/US2019/012696, 8 pages.
International Preliminary Report on Patentability dated Jul. 14, 2020 in PCT/US2019/012701, 8 pages.
International Search Report and Written Opinion dated Sep. 4, 2019 in PCT/US2019/012701, 12 pages.
International Search Report and Written Opinion dated Sep. 6, 2019 in PCT/US2019/012696, 12 pages.
Jia, (2008). "A Guide to Pass the National Licensed Pharmacist Examination in Medicinal Chemistry," pp. 4-11,9 pages, English abstract.
Kamran et al., (2016). "Radioprotective Agents: Strategies and Translational Advances," Medicinal Research Reviews, 36(3):461-493, 33 pages.
Kim et al., (2016). "Whole Brain Radiotherapy and RRx-001: Two Partial Responses in Radioresistant Melanoma Brain Metastases from a Phase 1/11 Clinical Trial: A TITE-CRM Phase 1/11 Clinical Trial," Translational Oncology, 9(2):108-113.
Li, (2014). "Nursing Comprehensive Skills Training," China Press of Traditional Chinese Medicine, 3 pages, English abstract.
Miller et al., (2015). "CD47 Receptor Globally Regulates Metabolic Pathways That Control Resistance to Ionizing Radiation," J. Biol. Chern., 290:24858-24874.
Ning et al., (2002). "The Antiangiogenic Agents SU5416 and SU6668 Increase the Antitumor Effects of Fractionated Irradiation," Radiation Research, 157:5-51.
Ning et al., (2015). "Nrf2 activity as a potential biomarker for the pan-epigenetic anticancer agent, RRx-001," Oncotarget, 6(25):21547-21556.
Office Action received for U.S. Appl. No. 12/397,651 dated Feb. 11, 2011, 10 pages.
Office Action received for U.S. Appl. No. 12/397,651 dated Feb. 23, 2012, 8 pages.
Office Action received for U.S. Appl. No. 13/655,618 dated Feb. 25, 2014, 6 pages.
Office Action received for U.S. Appl. No. 13/655,618 dated May 2, 2013, 9 pages.
Office Action received for U.S. Appl. No. 14/849,783 mailed on Jan. 15, 2016, 5 pages.
Office Action received for U.S. Appl. No. 14/965,062 dated Aug. 11, 2016, 10 pages.
Office Action received for U.S. Appl. No. 14/965,062 dated Dec. 18, 2017, 8 pages.
Office Action received for U.S. Appl. No. 15/298,735 dated Aug. 30, 2018, 9 pages.
Office Action received for U.S. Appl. No. 15/669,403 mailed on Sep. 14, 2018, 9 pages.
Office Action received for U.S. Appl. No. 15/989,862 dated Feb. 8, 2019, 6 pages.
Office Action received for U.S. Appl. No. 16/284,035 dated Apr. 13, 2021, 17 pages.
Office Action received for U.S. Appl. No. 16/353,047 dated Aug. 31, 2020, 7 pages.
Office Action received for U.S. Appl. No. 16/712,148 dated Oct. 7, 2020, 7 pages.
Office Action received for U.S. Appl. No. 16/960,443 dated May 28, 2021, 25 pages.
Oronsky et al., (2016). "RRx-001, A novel dinitroazetidine radiosensitizer," Invest. New Drugs, 34(3):371-377, 7 pages.
Pinkel, (1958). "The use of body surface area as a criterion of drug dosage in cancer chemotherapy," Cancer Research, 18:853-856.
Rafikova et al., (2004). "Control of Plasma Nitric Oxide Bioactivity by Perfluorocarbons Physiological Mechanisms and Clinical Implications," Circulation., 110:3573-3580.
Reid et al., (2014). "Two Case Reports of Resensitization to Previous Chemotherapy with the Novel Hypoxia-Activated Hypomethylating Anticancer Agent RRx-001 in Metastatic Colorectal Cancer Patients," Case Rep. Oncol., 7(1):79-85.
Reid et al., (2015). "Safety and activity of RRx-001 in patients with advanced cancer: a first-in-human, open-label, dose-escalation phase 1 study," Lancet Oncol, 16:1133-42.

(56) References Cited

OTHER PUBLICATIONS

Rupnow et al., (1998). "p53 Mediates Apoptosis Induced by C-Myc Activation in Hypoxic or Gamma Irradiated Fibroblasts," Cell Death and Differentiation, 7:141-147.
Scicinski et al., (2014). "Development of methods for the bioanalysis of RRx-001 and metabolites", Bioanalysis, 6(7):947-956.
Scicinski et al., (2015). "No to cancer: The complex and multifaceted role of nitric oxide and the epigenetic nitric oxide donor, RRx-001," Redox Biology, 6:1-8.
Thomas, (2016). "Mucositis in Cancer Patients: A Review," available online at <https://www.uspharmacist.com/article/mucositis-in-cancer-patients-a-review#:~:text=Mucositis%20is%20a%20common%20complication,the%20gastrointestinga%20(GI)%20tract.&text=Although%20mucositis%20can%20occur%20anywhere,site%22is%20the%20oral%20cavity>, 10 pages.
Yamaguchi, A., et al., "Photodynamic Therapy with Motexafin Lutetium (Lu-Tex) Reduces Experimental Graft Coronary Artery Disease," Transplantation, Jun. 15, 2001, pp. 1526-1532, vol. 71, No. 11, 11 pages.
You, (2011). " 代动力学性质., 不但增加了血药浓度,, 且延长作用时间 ," Medicinal Chemistry, pp. 585-588, 5 pages English abstract.
Zervoudakis et al., (2017). "Treatment Options in Colorectal Liver Metastases: Hepatic Arterial Infusion," Vise Med, 33:47-53.
Zuo, (2015). "Chapter 16: Cell Death," Medical Cell Biology, pp. 230-235, 7 pages English abstract.

\* cited by examiner

COMPOSITIONS AND METHODS FOR INTRAVENOUS ADMINISTRATION OF 2-BROMO-1-(3,3-DINITROAZETIDIN-1-YL) ETHANONE

CROSS REFERENCE TO RELATED APPLICATION

This application is a U.S. national stage application under 35 U.S.C. § 371 of International Application No. PCT/US2017/012948, filed on Jan. 11, 2017, which claims the benefit of and priority to U.S. Patent Application No. 62/277,236, filed on Jan. 11, 2016, the contents of each of which are hereby incorporated by reference herein.

FIELD OF THE INVENTION

The invention provides compositions and methods for intravenous administration of 2-bromo-1-(3,3-dinitroazetidin-1-yl)ethanone (ABDNAZ), including formulations containing autologous whole blood and ABDNAZ that can be rapidly administered to a patient by intravenous infusion without any significant pain at the site of infusion.

BACKGROUND

Cancer is a significant health problem despite the many advances made for detecting and treating this disease. Leading types of cancer afflicting substantial numbers of patients include prostate cancer, breast cancer, and lung cancer. Prostate cancer is the most common form of cancer among males, with an estimated incidence of 30% in men over the age of 50. Moreover, clinical evidence indicates that human prostate cancer has the propensity to metastasize to bone, and the disease appears to progress inevitably from androgen dependent to androgen refractory status, leading to increased patient mortality. Breast cancer remains a leading cause of death in women. Its cumulative risk is relatively high; certain reports indicate that approximately one in eight women are expected to develop some type of breast cancer by age 85 in the United States. Likewise, lung cancer is a leading cause of cancer-related death, and non-small cell lung cancer (NSCLC) accounts for about 80% of these cases.

Treatment options for cancer patients often include surgery, radiotherapy, chemotherapy, hormone therapy, or a combination thereof. The compound ABDNAZ described in, for example, U.S. Pat. Nos. 7,507,842; 8,299,053; and 8,927,527 has been studied in multiple clinical trials for use in treating cancer. ABDNAZ is typically formulated as a mixture with water, dimethylacetamide, and a poly(ethylene glycol) for intravenous infusion to the patient suffering from cancer. In clinical trials, patients receiving the aforementioned mixture of ABDNAZ by intravenous infusion have complained of significant pain at the site of infusion due to the ABDNAZ mixture. The significant pain at the site of infusion due to the ABDNAZ mixture has required medical personnel to reduce the rate at which the ABDNAZ mixture is administered to the patient, sometimes requiring infusion times up to eight hours. The long infusion times and slow rate of administration has, in some instances, limited the amount of ABDNAZ that can be administered to a patient when the ABDNAZ is used in combination with radiation therapy to be performed the same day as administration of ABDNAZ.

The present invention provides a new formulation containing ABDNAZ that can be rapidly administered to the patient without causing any significant pain at the site of infusion and has other advantages as described herein below.

SUMMARY

The invention provides compositions and methods for intravenous administration of 2-bromo-1-(3,3-dinitroazetidin-1-yl)ethanone (ABDNAZ), including formulations containing autologous whole blood and ABDNAZ that can be rapidly administered to a patient by intravenous infusion. The compositions and methods provide the further advantage that rapid administration of the formulation does not result in any significant pain at the site of intravenous infusion due to the administration. The compound ABDNAZ has the following chemical structure:

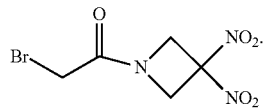

The ABDNAZ formulations contain whole blood (preferably autologous whole blood), ABDNAZ, and an anticoagulant. The formulations and methods are particularly useful for administering ABDNAZ to a patient suffering from cancer. The ABDNAZ formulations can be administered intravenously to the patient at a rate of, for example, at least 5 mL/hour, 10 mL/hour, 30 mL/hour, or higher rates. The rapid rate of administration reduces the time required to administer a therapeutically effective amount of ABDNAZ for treating cancer, and has particular advantages when large doses of ADBDNAZ need to be administered to the patient during the same day as the patient receives radiation therapy. The methods can be further characterized according to the magnitude of pain experienced by the patient at the site of administering the ABDNAZ formulation, wherein the magnitude of any pain experienced by the patient is small. The invention having been generally described is explained in more detail in the aspects and embodiments below and in the detailed description.

One aspect of the invention provides a method for intravenous administration of an ABDNAZ formulation to a patient suffering from cancer in order to treat the cancer. The method comprises intravenously administering to the patient in need thereof a therapeutically effective amount of an ABDNAZ formulation described herein (such as a formulation comprising whole blood, ABDNAZ, and an anticoagulant) in order to treat the cancer. The ABDNAZ formulation may be administered at a rate of, for example, at least 5 mL/hour or at least 10 mL/hour. The method provides the advantage of being able to rapidly administer ABDNAZ without causing undue pain at the site of administering the ABDNAZ formulation, and any such pain may be characterized according to, for example, the feature that any such pain is no greater than Grade 1 pain.

Another aspect of the invention provides a method for rapid intravenous administration of an ABDNAZ formulation to a patient while minimizing injection site pain experienced by the patient, wherein the method comprises intravenously administering to the patient at a rate of, for example, at least 10 mL/hour, an ABDNAZ formulation described herein (such as a formulation comprising whole blood, ABDNAZ, and an anticoagulant), wherein any pain experienced by the patient at the site of intravenous administration of the ABDNAZ formulation due to intravenous administration of the ABDNAZ formulation is no greater than Grade 2. The ABDNAZ formulation may be further characterized according to the concentration of ABDNAZ in the formulation, such as where the formulation contains ABDNAZ at a concentration of, for example, at least 10 μg/mL, at least 20 μg/mL, at least 50 μg/mL, at least 100 μg/mL, or at least 150 μg/mL.

Another aspect of the invention provides an intravenous formulation containing ABDNAZ for intravenous administration to a patient, wherein the formulation comprises: (a) whole blood in an amount of at least 60% v/v of the formulation; (b) a polyethylene glycol at a concentration of from about 0.4 μL/mL to about 30 μL/mL in the formulation; (c) N,N-dimethylacetamide at a concentration of from about 0.2 μL/mL to about 15 μL/mL in the formulation; (d) ABDNAZ at a concentration of at least 10 μg/mL in the formulation; (e) water; and (f) an anticoagulant. The intravenous formulations are suited for use in the methods described herein, and provide the advantage of being able to be rapidly administered to the patient by intravenous infusion without causing any significant pain at the site of administration.

Another aspect of the invention provides a kit for intravenous administration of an ABDNAZ formulation to a patient suffering from cancer in order to treat the cancer. The kit comprises: (i) a formulation comprising ABDNAZ, and (ii) instructions for intravenous administration of an ABDNAZ formulation to a patient suffering from cancer in order to treat the cancer according to procedures described herein. One benefit of the kit is that it provides an ABDNAZ formulation capable of being rapidly administered to the patient by intravenous infusion without causing any significant pain at the site of administration.

Another aspect of the invention provides a kit for rapid intravenous administration of an ABDNAZ formulation to a patient while minimizing injection site pain experienced by the patient. The kit comprises: (i) a formulation comprising ABDNAZ, and (ii) instructions for rapid intravenous administration of an ABDNAZ formulation to a patient while minimizing injection site pain experienced by the patient according to procedures described herein.

DETAILED DESCRIPTION

The invention provides compositions and methods for intravenous administration of 2-bromo-1-(3,3-dinitroazetidin-1-yl)ethanone (ABDNAZ), including formulations containing autologous whole blood and ABDNAZ that can be rapidly administered to a patient by intravenous infusion. The compositions and methods provide the further advantage that rapid administration of the formulation does not result in any significant pain at the site of intravenous infusion due to the administration.

The ABDNAZ formulations contain whole blood (preferably autologous whole blood), ABDNAZ, and an anticoagulant. The formulations and methods are particularly useful for administering ABDNAZ to a patient suffering from cancer. The ABDNAZ formulations can be administered intravenously to the patient at a rate of, for example, at least 5 mL/hour, 10 mL/hour, 30 mL/hour, or a higher rate. The rapid rate of administration reduces the time required to administer a therapeutically effective amount of ABDNAZ for treating cancer, and has particular advantages when large doses of ADBNAZ need to be administered to the patient during the same day as the patient receives radiation therapy. The methods can be further characterized according to the magnitude of pain experienced by the patient at the site of administering the ABDNAZ formulation, wherein the magnitude of any pain experienced by the patient is small. Various aspects of the invention are set forth below in sections; however, aspects of the invention described in one particular section are not to be limited to any particular section.

I. Therapeutic Methods

The invention provides methods for intravenous administration of 2-bromo-1-(3,3-dinitroazetidin-1-yl)ethanone (ABDNAZ). The methods enable more rapid administration of ABDNAZ to a patient and avoid any substantial pain at the site of administration due to the ABDNAZ. Various features of the methods are described in sections below. The sections are arranged for convenience and information in one section is not limited to that section, but may be applied to other sections.

First Method

One aspect of the invention provides a method for intravenous administration of an ABDNAZ formulation to a patient suffering from cancer in order to treat the cancer. The method comprises intravenously administering to the patient in need thereof a therapeutically effective amount of an ABDNAZ formulation comprising whole blood, ABDNAZ, and an anticoagulant, in order to treat the cancer. The whole blood is preferably autologous whole blood.

The method may be further characterized according to the rate at which the ABDNAZ formulation is intravenously administered to the patient. In certain embodiments, the ABDNAZ formulation is intravenously administered to the patient at a rate of at least 3 mL/hour. In certain embodiments, the ABDNAZ formulation is intravenously administered to the patient at a rate of at least 5 mL/hour. In certain embodiments, wherein the ABDNAZ formulation is intravenously administered to the patient at a rate of at least 10 mL/hour.

One benefit of the above method is that it substantially reduces the amount of pain experienced by the patient at the site of administering ABDNAZ. Accordingly, in certain embodiments, the method is characterized by the feature that any pain experienced by the patient at the site of intravenous administration of the ABDNAZ formulation due to intravenous administration of the ABDNAZ formulation is no greater than Grade 2. In certain other embodiments, any pain experienced by the patient at the site of intravenous administration of the ABDNAZ formulation due to intravenous administration of the ABDNAZ formulation is no greater than Grade 1.

Second Method

Another aspect of the invention provides a method for intravenous administration of an ABDNAZ formulation to a patient while minimizing injection site pain experienced by the patient. The method comprises intravenously administering to the patient at a rate of at least 3 mL/hour an ABDNAZ formulation comprising whole blood, ABDNAZ, and an anticoagulant, wherein any pain experienced by the patient at the site of intravenous administration of the ABDNAZ formulation due to intravenous administration of the ABDNAZ formulation is no greater than Grade 2. In certain embodiments, the ABDNAZ formulation is intravenously administered to the patient at a rate of at least 5 mL/hour.

Third Method

Another aspect of the invention provides a method for rapid intravenous administration of an ABDNAZ formulation to a patient while minimizing injection site pain experienced by the patient. The method comprises intravenously administering to the patient at a rate of at least 10 mL/hour an ABDNAZ formulation comprising whole blood, ABDNAZ, and an anticoagulant, wherein any pain experienced by the patient at the site of intravenous administration of the ABDNAZ formulation due to intravenous administration of the ABDNAZ formulation is no greater than Grade 2.

One benefit of the above method is that it substantially reduces the amount of pain experienced by the patient at the site of administering ABDNAZ. Accordingly, in certain embodiments, the method is characterized by the feature that any pain experienced by the patient at the site of intravenous administration of the ABDNAZ formulation due to intravenous administration of the ABDNAZ formulation is no greater than Grade 1.

In certain embodiments, the patient is suffering from cancer.

Fourth Method

Another aspect of the invention provides a method for intravenous administration of an ABDNAZ formulation to a patient while minimizing injection site pain experienced by the patient. The method comprises intravenously administering to the patient at a rate of at least 3 mL/hour an ABDNAZ formulation comprising ABDNAZ, an anticoagulant, and a blood product selected from the group consisting of an erythrocyte cell, blood plasma, and whole blood. The method may be further characterized according to the feature that any pain experienced by the patient at the site of intravenous administration of the ABDNAZ formulation due to intravenous administration of the ABDNAZ formulation is no greater than Grade 2. In certain embodiments, the ABDNAZ formulation is intravenously administered to the patient at a rate of at least 5 mL/hour, or at least 10 mL/hour. In certain embodiments, the blood product is an erythrocyte cell. In certain embodiments, the ABDNAZ formulation comprises a population of erythrocyte cells, such as where the ABDNAZ formulation comprises erythrocyte cells in an amount of at least about 2%, 5%, 8%, 10%, 15%, 20%, 25%, 30%, 35%, 40%, or 45% by volume of the ABDNAZ formulation.

Exemplary Features of the First, Second, Third, and Fourth Methods

The above methods may be further characterized by additional features, such as the rate of infusion of the ABDNAZ formulation, the concentration of ABDNAZ in the ABDNAZ formulation, the identity of components in the ABDNAZ formulation, the amount of whole blood in the ABDNAZ formulation, the volume of ABDNAZ formulation administered to patient, and other features as described in more detail below.

Rate of Infusion of ABDNAZ Formulation

The method may be further characterized according to the rate at which the ABDNAZ formulation is administered to the patient. Accordingly, in certain embodiments, the ABDNAZ formulation is intravenously administered to the patient at a rate of at least 30 mL/hour. In certain embodiments, the ABDNAZ formulation is intravenously administered to the patient at a rate of at least 60 mL/hour. In certain embodiments, the ABDNAZ formulation is intravenously administered to the patient at a rate of at least 90 mL/hour. In certain embodiments, the ABDNAZ formulation is intravenously administered to the patient at a rate of at least 120 mL/hour. In yet other embodiments, the ABDNAZ formulation is intravenously administered to the patient at a rate of at least 150 mL/hour, 180 mL/hour, 210 mL/hour, 240 mL/hour, 270 mL/hour, 300 mL/hour, 330 mL/hour, or 360 mL/hour. In yet other embodiments, the ABDNAZ formulation is intravenously administered to the patient at a rate in the range of from about 100 mL/hour to about 150 mL/hour, from about 150 mL/hour to about 200 mL/hour, from about 180 mL/hour to about 220 mL/hour, from about 200 mL/hour to about 250 mL/hour, from about 250 mL/hour to about 300 mL/hour, from about 275 mL/hour to about 325 mL/hour, or from about 300 mL/hour to about 350 mL/hour.

Concentration of ABDNAZ in the ABDNAZ Formulation

The method may be further characterized according to the concentration of ABDNAZ in the ABNDAZ formulation. Accordingly, in certain embodiments, the ABDNAZ formulation contains ABDNAZ at a concentration of at least 10 µg/mL. In certain embodiments, the ABDNAZ formulation contains ABDNAZ at a concentration of at least 20 µg/mL. In certain embodiments, the ABDNAZ formulation contains ABDNAZ at a concentration of at least 50 µg/mL. In certain embodiments, the ABDNAZ formulation contains ABDNAZ at a concentration of at least 100 µg/mL. In certain embodiments, the ABDNAZ formulation contains ABDNAZ at a concentration of at least 150 µg/mL. In certain embodiments, the ABDNAZ formulation contains ABDNAZ at a concentration in the range of about 10 µg/mL to about 1 mg/mL. In certain embodiments, the ABDNAZ formulation contains ABDNAZ at a concentration in the range of about 10 µg/mL to about 0.5 mg/mL. In certain embodiments, the ABDNAZ formulation contains ABDNAZ at a concentration in the range of about 10 µg/mL to about 250 µg/mL. In certain embodiments, the ABDNAZ formulation contains ABDNAZ at a concentration in the range of about 20 µg/mL to about 200 µg/mL. In certain embodiments, the ABDNAZ formulation contains ABDNAZ at a concentration in the range of about 200 µg/mL to about 750 µg/mL. In certain embodiments, the ABDNAZ formulation contains ABDNAZ at a concentration in the range of about 200 µg/mL to about 400 µg/mL, about 400 µg/mL to about 600 µg/mL, about 500 µg/mL to about 700 µg/mL, or about 600 µg/mL to about 700 µg/mL.

Exemplary More Specific ABDNAZ Formulations

Exemplary more specific ABDNAZ formulations that may be used in the methods include, for example, formulations containing whole blood, ABDNAZ, an anticoagulant, and optionally one or more of water, a polyethylene glycol, and N,N-dimethylacetamide. In certain embodiments, the ABDNAZ formulation consists essentially of whole blood, ABDNAZ, and an anticoagulant. In certain embodiments, the ABDNAZ formulation consists of whole blood, ABDNAZ, an anticoagulant, and optionally one or more of water, a polyethylene glycol, and N,N-dimethylacetamide. In certain embodiments, the ABDNAZ formulation consists of whole blood, ABDNAZ, an anticoagulant, and optionally one or more of water, a polyethylene glycol having a number-average molecular weight in the range of about 200 g/mol to about 600 g/mol, and N,N-dimethylacetamide. In certain embodiments, the ABDNAZ formulation consists of whole blood, ABDNAZ, an anticoagulant, water, a polyethylene glycol having a number-average molecular weight in the range of about 200 g/mol to about 600 g/mol, and N,N-dimethylacetamide. In certain embodiments, the ABDNAZ formulation consists of whole blood, ABDNAZ, an anticoagulant, and optionally one or more of water, a polyethylene glycol having a number-average molecular weight of about 400 g/mol, and N,N-dimethylacetamide. In certain embodiments, the ABDNAZ formulation consists of whole blood, ABDNAZ, an anticoagulant, water, a polyethylene glycol having a number-average molecular weight of about 400 g/mol, and N,N-dimethylacetamide.

Anticoagulant

The method may be further characterized according to the identity and/or amount of the anticoagulant. Accordingly, in certain embodiments, the anticoagulant comprises one or more of heparin and a citrate salt. In certain embodiments, the anticoagulant is a solution comprising an alkali metal citrate salt, dextrose, and water. In certain embodiments, the anticoagulant is present in the ABDNAZ formulation in an amount ranging from about 0.1% wt/wt to about 15% w/w. In certain embodiments, the anticoagulant is present in the ABDNAZ formulation in an amount ranging from about 1% wt/wt to about 10% w/w. In certain embodiments, the anticoagulant is present in the ABDNAZ formulation in an amount ranging from about 2% wt/wt to about 8% w/w.

Amount of Whole Blood in the ABDNAZ Formulation

The method may be further characterized according to the amount of whole blood in the ABDNAZ formulation. Accordingly, in certain embodiments, the whole blood constitutes at least 30% wt/wt of the ABDNAZ formulation. In certain embodiments, the whole blood constitutes at least 40% wt/wt of the ABDNAZ formulation. In certain embodiments, the whole blood constitutes at least 50% wt/wt of the ABDNAZ formulation. In certain embodiments, the whole blood constitutes at least 60% wt/wt of the ABDNAZ formulation. In certain embodiments, the whole blood constitutes at least 75% wt/wt of the ABDNAZ formulation. In certain embodiments, the whole blood constitutes at least 90% wt/wt of the ABDNAZ formulation. In certain embodiments, the whole blood constitutes from about 60% wt/wt to about 99% wt/wt of the ABDNAZ formulation. In certain embodiments, the whole blood constitutes from about 70% wt/wt to about 95% wt/wt of the ABDNAZ formulation. In certain embodiments, the whole blood constitutes from about 75% wt/wt to about 90% wt/wt of the ABDNAZ formulation. In certain embodiments, there is from about 5 mL to about 10 mL of whole blood in the ABDNAZ formulation, from about 10 mL to about 15 mL of whole blood in the ABDNAZ formulation, from about 9 mL to about 11 mL of whole blood in the ABDNAZ formulation, from about 10 mL to about 20 mL of whole blood in the ABDNAZ formulation, from about 20 mL to about 30 mL of whole blood in the ABDNAZ formulation, from about 30 mL to about 50 mL of whole blood in the ABDNAZ formulation, from about 50 mL to about 70 mL of whole blood in the ABDNAZ formulation, or from about 70 mL to about 90 mL of whole blood in the ABDNAZ formulation. In certain embodiments, there is from about 90 mL to about 110 mL of whole blood in the ABDNAZ formulation. In certain embodiments, there is from about 95 mL to about 105 mL of whole blood in the ABDNAZ formulation. In certain embodiments, there is about 100 mL of whole blood in the ABDNAZ formulation.

Volume of ABDNAZ Formulation Administered to Patient

The method may be further characterized according to the volume of ABDNAZ formulation administered to the patient. Accordingly, in certain embodiments, the ABDNAZ formulation has a volume in the range of about 10 mL to about 200 mL. In certain embodiments, the ABDNAZ formulation has a volume in the range of about 10 mL to about 15 mL, about 15 mL to about 20 mL, about 20 mL to about 30 mL, or about 30 mL to about 50 mL. In certain embodiments, the ABDNAZ formulation has a volume in the range of about 50 mL to about 200 mL. In certain embodiments, the ABDNAZ formulation has a volume in the range of about 75 mL to about 150 mL. In certain embodiments, the ABDNAZ formulation has a volume in the range of about 90 mL to about 140 mL. In certain embodiments, the ABDNAZ formulation has a volume in the range of about 100 mL to about 140 mL. In certain embodiments, the ABDNAZ formulation has a volume in the range of about 100 mL to about 120 mL.

Timeline for Administering ABDNAZ Formulation

The method may be further characterized according to the timeline for administering the ABDNAZ formulation to the patient. Accordingly, in certain embodiments, intravenous administration of the ABDNAZ formulation commences within about 1 hour after formation of the ABDNAZ formulation. In certain embodiments, intravenous administration of the ABDNAZ formulation commences within about 30 minutes after formation of the ABDNAZ formulation. In certain embodiments, intravenous administration of the ABDNAZ formulation commences within about 20 minutes after formation of the ABDNAZ formulation. In certain embodiments, intravenous administration of the ABDNAZ formulation is complete within about 6 hours after formation of the ABDNAZ formulation. In certain embodiments, intravenous administration of the ABDNAZ formulation is complete within about 4 hours after formation of the ABDNAZ formulation.

Obtaining Whole Blood for ABDNAZ Formulation

The method may optionally further comprise obtaining an aliquot of whole blood from the patient, and then using said aliquot to prepare the ABDNAZ formulation for administration to the patient.

Location of Intravenous Administration

The method may be further characterized according to the location of intravenous administration to the patient. In certain embodiments, the intravenous administration is central intravenous administration. In certain embodiments, the intravenous administration is peripheral intravenous administration.

Dose of ABDNAZ Administered

Exemplary dosing amounts of ABDNAZ are provided according to the number of milligrams of ABDNAZ to be administered to the patient based on the surface area of the patient as measured in $m^2$. In certain embodiments, the dose ABDNAZ administered to the patient is from about $1\ mg/m^2$ to about $2\ mg/m^2$, about $2\ mg/m^2$ to about $4\ mg/m^2$, about $4\ mg/m^2$ to about $6\ mg/m^2$, about $6\ mg/m^2$ to about $8\ mg/m^2$, about $8\ mg/m^2$ to about $10\ mg/m^2$, about $10\ mg/m^2$ to about $12\ mg/m^2$, about $12\ mg/m^2$ to about $14\ mg/m^2$, about $14\ mg/m^2$ to about $16\ mg/m^2$, about $16\ mg/m^2$ to about $18\ mg/m^2$, about $18\ mg/m^2$ to about $20\ mg/m^2$, about $20\ mg/m^2$ to about $25\ mg/m^2$, about $25\ mg/m^2$ to about $30\ mg/m^2$, about $30\ mg/m^2$ to about $35\ mg/m^2$, about $35\ mg/m^2$ to about $40\ mg/m^2$, about $40\ mg/m^2$ to about $45\ mg/m^2$, about $45\ mg/m^2$ to about $50\ mg/m^2$, about $50\ mg/m^2$ to about $60\ mg/m^2$, or about $60\ mg/m^2$ to about $75\ mg/m^2$.

The dose of ABDNAZ administered to the patient may be further characterized according to both the amount of ABDNAZ and the mode of delivery, such as intravenous infusion. Accordingly, in certain embodiments, each dose of the formulation comprising ABDNAZ is administered to the patient by intravenous infusion providing ABDNAZ in an amount ranging from about $1\ mg/m^2$ to about $90\ mg/m^2$. In certain embodiments, each dose of the formulation comprising ABDNAZ is administered to the patient by intravenous infusion providing ABDNAZ in an amount ranging from about $1\ mg/m^2$ to about $10\ mg/m^2$. In certain embodiments, each dose of the formulation comprising ABDNAZ is administered to the patient by intravenous infusion providing ABDNAZ in an amount ranging from about $1\ mg/m^2$ to about $2.5\ mg/m^2$. In certain embodiments, each dose of the formulation comprising ABDNAZ is administered to the patient by intravenous infusion providing ABDNAZ in an amount ranging from about 2.5 mg/m² to about 5 mg/m². In certain embodiments, each dose of the formulation comprising ABDNAZ is administered to the patient by intravenous infusion providing ABDNAZ in an amount ranging from about 5 mg/m² to about 10 mg/m². In certain embodiments, each dose of the formulation comprising ABDNAZ is administered to the patient by intravenous infusion providing ABDNAZ in an amount ranging from about 5 mg/m² to about 7 mg/m². In certain embodiments, each dose of the formulation comprising ABDNAZ is administered to the patient by intravenous infusion providing ABDNAZ in an amount ranging from about 8 mg/m² to about 9 mg/m². In certain embodiments, each dose of the formulation comprising ABDNAZ is administered to the patient by intravenous infusion providing ABDNAZ in an amount ranging from about 10 mg/m² to about 20 mg/m². In certain embodiments, each dose of the formulation comprising ABDNAZ is administered to the patient by intravenous infusion providing ABDNAZ in an amount ranging from about 1 mg/m² to about 1.5 mg/m², about 1.5 mg/m² to about 2 mg/m², about 2 mg/m² to about 2.5 mg/m², about 2.5 mg/m² to about 3 mg/m², about 3 mg/m² to about 3.5 mg/m², about 3.5 mg/m² to about 4 mg/m², about 4 mg/m² to about 4.5 mg/m², about 4.5 mg/m² to about 5 mg/m², about 5 mg/m² to about 5.5 mg/m², about 5.5 mg/m² to about 6 mg/m², about 6 mg/m² to about 6.5 mg/m², about 6.5 mg/m² to about 7 mg/m², about 7 mg/m² to about 7.5 mg/m², about 7.5 mg/m² to about 8 mg/m², about 8 mg/m² to about 8.5 mg/m², about 8.5 mg/m² to about 9 mg/m², about 9 mg/m² to about 9.5 mg/m², about 9.5 mg/m² to about 10 mg/m², about 10 mg/m² to about 12 mg/m², about 12 mg/m² to about 14 mg/m², about 14 mg/m² to about 16 mg/m², about 16 mg/m² to about 18 mg/m², about 18 mg/m² to about 20 mg/m², about 20 mg/m² to about 25 mg/m², about 25 mg/m² to about 30 mg/m², about 30 mg/m² to about 35 mg/m², about 35 mg/m² to about 40 mg/m², about 40 mg/m² to about 45 mg/m², or about 45 mg/m² to about 50 mg/m². In certain embodiments, each dose of the formulation comprising ABDNAZ is administered to the patient by intravenous infusion providing ABDNAZ in an amount ranging from about 3 mg/m² to about 8 mg/m².

In more specific embodiments, each dose of the formulation comprising ABDNAZ is administered to the patient by intravenous infusion providing ABDNAZ in an amount of about 1.25 mg/m². In certain embodiments, each dose of the formulation comprising ABDNAZ is administered to the patient by intravenous infusion providing ABDNAZ in an amount of about 2.5 mg/m². In certain embodiments, each dose of the formulation comprising ABDNAZ is administered to the patient by intravenous infusion providing ABDNAZ in an amount of about 5 mg/m². In certain embodiments, each dose of the formulation comprising ABDNAZ is administered to the patient by intravenous infusion providing ABDNAZ in an amount of about 8.4 mg/m². In certain embodiments, each dose of the formulation comprising ABDNAZ is administered to the patient by intravenous infusion providing ABDNAZ in an amount of about 1 mg/m², about 1.5 mg/m², about 2 mg/m², about 2.5 mg/m², about 3 mg/m², about 3.5 mg/m², about 4 mg/m², about 4.5 mg/m², about 5 mg/m², about 5.5 mg/m², about 6 mg/m², about 6.5 mg/m², about 7 mg/m², about 7.5 mg/m², about 8 mg/m², about 8.5 mg/m², about 9 mg/m², about 9.5 mg/m², about 10 mg/m², about 12 mg/m², about 14 mg/m², about 16 mg/m², about 18 mg/m², about 20 mg/m², about 25 mg/m², about 30 mg/m², about 35 mg/m², about 40 mg/m², about 45 mg/m², or about 50 mg/m².

Extent of any Pain at Site of Intravenous Administration

The method may be further characterized according to the extent of any pain experienced by the patient at the site of intravenous administration of the ABDNAZ formulation due to intravenous administration of the ABDNAZ formulation. Accordingly, in certain embodiments, any pain experienced by the patient at the site of intravenous administration of the ABDNAZ formulation due to intravenous administration of the ABDNAZ formulation is no greater than Grade 2. In certain other embodiments, any pain experienced by the patient at the site of intravenous administration of the ABDNAZ formulation due to intravenous administration of the ABDNAZ formulation is no greater than Grade 1. The Grade scale for evaluating pain is art-recognized and ranges from 0 to 5, with zero being no pain and five being intense pain. General description of the pain Grades is provided in the table below.

| Grade of Pain | General Description |
| --- | --- |
| 0 | No Pain |
| 1 | Barely noticeable pain |
| 2 | Mild pain |
| 3 | Moderate pain |
| 4 | Very painful |
| 5 | Intense pain that is very difficult to withstand for greater than 5 minutes. |

Type of Cancer

When the ABDNAZ formulation is being administered to a patient suffering from cancer in order to treat the cancer, the method may be further characterized according to type of cancer to be treated. For example, in certain embodiments, the cancer is a solid tumor. In certain embodiments, the cancer is brain cancer, bladder cancer, breast cancer, cervical cancer, cholangiocarcinoma, colon cancer, colorectal cancer, endometrial cancer, esophageal cancer, lung cancer, liver cancer, melanoma, ovarian cancer, pancreatic cancer, prostate cancer, rectal cancer, renal cancer, stomach cancer, testicular cancer, or uterine cancer. In certain embodiments, the cancer is brain cancer. In certain embodiments, the cancer is colorectal cancer. In certain embodiments, the cancer is cholangiocarcinoma or lung cancer.

In certain embodiments, the cancer is lung cancer. In certain embodiments, the lung cancer is small cell lung cancer. In certain other embodiments, the cancer is non-small cell lung cancer. In certain embodiments, the cancer is a leukemia or lymphoma. In certain embodiments, the cancer is a B-cell lymphoma or non-Hodgkin lymphoma.

Additional exemplary cancers for treatment include, for example, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, and uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

Characterization of Anti-Cancer Effects

When the ABDNAZ formulation is being administered to a cancer patient in order to treat the cancer, the therapeutic method may be further characterized according to the anti-cancer effect of the treatment, such as (i) a reduction in the size of at least one tumor in the patient, and/or (ii) reduction in the number of tumors in the patient.

Accordingly, in certain embodiments, the therapeutic method is characterized by at least a 20% reduction in the size of at least one tumor in the patient. In certain other embodiments, there is at least a 35% reduction in the size of at least one tumor in the patient. In certain other embodiments, there is at least a 50% reduction in the size of at least one tumor in the patient. In certain other embodiments, there is at least a 60%, 70%, 80% or 90% reduction in the size of at least one tumor in the patient. In certain other embodiments, there is about a 5%-50%, 10%-50%, 20%-50%, 5%-75%, 10%-75%, 20%-75%, or 50%-90% reduction in the size of at least one tumor in the patient.

When the cancer to be treated is a brain metastases, the method may be further characterized according to the reduction in number and/or size of the brain metastases. In certain embodiments, there is at least a 20% reduction in the number of brain metastases in the patient. In certain other embodiments, there is at least a 35% reduction in the number of brain metastases in the patient. In yet other embodiments, there is at least a 50% reduction in the number of brain metastases in the patient. In certain other embodiments, there is at least a 60%, 70%, 80% or 90% reduction in the number of brain metastases in the patient. In certain other embodiments, there is about a 5%-50%, 10%-50%, 20%-50%, 5%-75%, 10%-75%, 20%-75%, or 50%-90% reduction in the number of brain metastases in the patient.

Patients for Treatment

The therapeutic method may be further characterized according to the patient to be treated. In certain embodiments, the patient is an adult human. In certain other embodiments, the patient is a pediatric human.

In certain embodiments, the patient does not suffer from anemia or have reduced blood volume. In certain embodiments, the patient has at least 95% of the amount of their average daily blood volume.

Form of ABDNAZ

In certain embodiments, the patient may be administered a pharmaceutically acceptable salt of ABDNAZ.

III. Exemplary More Specific ABDNAZ Formulations

One exemplary more specific formulation is an intravenous formulation containing ABDNAZ for intravenous administration to a patient, comprising:
 a. whole blood in an amount of at least 60% v/v of the formulation;
 b. a polyethylene glycol at a concentration of from about 0.4 µL/mL to about 30 µL/mL in the formulation;
 c. N,N-dimethylacetamide at a concentration of from about 0.2 µL/mL to about 15 µL/mL in the formulation;
 d. ABDNAZ at a concentration of at least 10 µg/mL in the formulation;
 e. water; and
 f. an anticoagulant.

Another exemplary more specific formulation is a formulation that consists essentially of:
 a. whole blood in an amount of at least 60% v/v of the formulation;
 b. a polyethylene glycol at a concentration of from about 0.4 µL/mL to about 30 µL/mL in the formulation;
 c. N,N-dimethylacetamide at a concentration of from about 0.2 µL/mL to about 15 µL/mL in the formulation;
 d. ABDNAZ at a concentration of at least 10 µg/mL in the formulation;
 e. water; and
 f. an anticoagulant.

Another exemplary more specific formulation is a formulation that consists of:
 a. whole blood in an amount of at least 60% v/v of the formulation;
 b. a polyethylene glycol at a concentration of from about 0.4 µL/mL to about 30 µL/mL in the formulation;
 c. N,N-dimethylacetamide at a concentration of from about 0.2 µL/mL to about 15 µL/mL in the formulation;
 d. ABDNAZ at a concentration of at least 10 µg/mL in the formulation;
 e. water; and
 f. an anticoagulant.

Another exemplary more specific formulation is an intravenous formulation containing ABDNAZ for intravenous administration to a patient, comprising:

a. a blood product (e.g., an erythrocyte cell, blood plasma, or whole blood) in an amount of at least 30% v/v of the formulation;
  b. optionally a polyethylene glycol at a concentration of from about 0.4 µL/mL to about 30 µL/mL in the formulation;
  c. optionally N,N-dimethylacetamide at a concentration of from about 0.2 µL/mL to about 15 µL/mL in the formulation;
  d. ABDNAZ at a concentration of at least 10 µg/mL in the formulation;
  e. optionally water; and
  f. optionally an anticoagulant.

Another exemplary more specific formulation is an intravenous formulation containing ABDNAZ for intravenous administration to a patient, comprising:
  a. whole blood in an amount of at least 30% v/v of the formulation;
  b. a polyethylene glycol (e.g., at a concentration of from about 0.4 µL/mL to about 30 µL/mL in the formulation);
  c. N,N-dimethylacetamide (e.g., at a concentration of from about 0.2 µL/mL to about 15 µL/mL in the formulation);
  d. ABDNAZ at a concentration of at least 10 µg/mL in the formulation;
  e. water; and
  f. an anticoagulant.

Another exemplary more specific formulation is a formulation that consists essentially of:
  a. whole blood in an amount of at least 30% v/v of the formulation;
  b. a polyethylene glycol (e.g., at a concentration of from about 0.4 µL/mL to about 30 µL/mL in the formulation);
  c. N,N-dimethylacetamide (e.g., at a concentration of from about 0.2 µL/mL to about 15 µL/mL in the formulation);
  d. ABDNAZ at a concentration of at least 10 µg/mL in the formulation;
  e. water; and
  f. an anticoagulant.

Exemplary Features of Intravenous Formulation

The intravenous formulation may be characterized according to, for example, the identity of a polyethylene glycol, anticoagulant, concentration of ABDNAZ, amount of whole blood and other features described herein below.

Polyethylene Glycol

The formulation may be further characterized according to the identity of a polyethylene glycol in the ABDNAZ formulation. Accordingly, in certain embodiments, the polyethylene glycol is a polyethylene glycol having a number-average molecular weight in the range of about 200 g/mol to about 600 g/mol. In certain embodiments, the polyethylene glycol is a polyethylene glycol having a number-average molecular weight of about 400 g/mol.

In certain embodiments, the polyethylene glycol is present at a concentration of from about 0.4 µL/mL to about 4 µL/mL in the formulation. In certain embodiments, the N,N-dimethylacetamide at a concentration of from about 0.2 µL/mL to about 2 µL/mL in the formulation.

Anticoagulant

The formulation may be further characterized according to the identity of an anticoagulant in the ABDNAZ formulation. Accordingly, in certain embodiments, the anticoagulant comprises one or more of heparin and a citrate salt. In certain embodiments, the anticoagulant is a solution comprising an alkali metal citrate salt, dextrose, and water.

Concentration of ABDNAZ

The formulation may be further characterized according to the concentration of ABDNAZ in the ABDNAZ formulation. Accordingly, in certain embodiments, the ABDNAZ formulation contains ABDNAZ at a concentration of at least 20 µg/mL. In certain embodiments, the ABDNAZ formulation contains ABDNAZ at a concentration of at least 50 µg/mL. In certain embodiments, the ABDNAZ formulation contains ABDNAZ at a concentration of at least 100 µg/mL. In certain embodiments, the ABDNAZ formulation contains ABDNAZ at a concentration of at least 150 µg/mL. In certain embodiments, the ABDNAZ formulation contains ABDNAZ at a concentration in the range of about 10 µg/mL to about 1 mg/mL. In certain embodiments, the ABDNAZ formulation contains ABDNAZ at a concentration in the range of about 10 µg/mL to about 0.5 mg/mL. In certain embodiments, the ABDNAZ formulation contains ABDNAZ at a concentration in the range of about 10 µg/mL to about 250 µg/mL. In certain embodiments, the ABDNAZ formulation contains ABDNAZ at a concentration in the range of about 20 µg/mL to about 200 µg/mL.

Amount of Whole Blood

The formulation may be further characterized according to the amount of whole blood in the ABDNAZ formulation. Accordingly, in certain embodiments, the whole blood constitutes at least 30% wt/wt of the formulation. In certain embodiments, the whole blood constitutes at least 40% wt/wt of the formulation. In certain embodiments, the whole blood constitutes at least 50% wt/wt of the formulation. In certain embodiments, the whole blood constitutes at least 75% wt/wt of the formulation. In certain embodiments, the whole blood constitutes at least 90% wt/wt of the formulation. In certain embodiments, the whole blood constitutes from about 60% wt/wt to about 99% wt/wt of the formulation. In certain embodiments, the whole blood constitutes from about 70% wt/wt to about 95% wt/wt of the formulation. In certain embodiments, the whole blood constitutes from about 75% wt/wt to about 90% wt/wt of the formulation. In certain embodiments, there is from about 90 mL to about 110 mL of whole blood in the formulation. In certain embodiments, wherein there is from about 95 mL to about 105 mL of whole blood in the formulation. In certain embodiments, there is about 100 mL of whole blood in the formulation.

Unit Dose Form of Intravenous Formulation

The formulation may be further characterized according to the volume of a unit dose of the ABDNAZ formulation. Accordingly, in certain embodiments, the formulation is in the form of a unit dose having a volume in the range of about 10 mL to about 200 mL. In certain embodiments, the formulation is in the form of a unit dose having a volume in the range of about 10 mL to about 15 mL, about 15 mL to about 20 mL, about 20 mL to about 30 mL, about 30 mL to about 40 mL, or about 40 mL to about 50 mL. In certain embodiments, the formulation is in the form of a unit dose having a volume in the range of about 50 mL to about 200 mL. In certain embodiments, the formulation is in the form of a unit dose having a volume in the range of about 75 mL to about 150 mL. In certain embodiments, the formulation is in the form of a unit dose having a volume in the range of about 90 mL to about 140 mL. In certain embodiments, the formulation is in the form of a unit dose having a volume in the range of about 100 mL to about 140 mL. In certain embodiments, the formulation is in the form of a unit dose having a volume in the range of about 100 mL to about 120 mL.

Characterization of Pain Effect Upon Intravenous Administration to Patient

The formulation may be further characterized according to the extent of pain experienced by the patient upon intravenous administration of the ABDNAZ formulation to the patient. Accordingly, in certain embodiments, the formulation is characterized by the feature that any pain experienced by the patient at the site of intravenous administration due to intravenous administration of the formulation to the patient at a rate in the range of 10 mL/hour to 50 mL/hour is no greater than Grade 2. In certain embodiments, wherein the formulation is characterized by the feature that any pain experienced by the patient at the site of intravenous administration due to intravenous administration of the formulation to the patient at a rate in the range of 10 mL/hour to 50 mL/hour is no greater than Grade 1.

The description above describes multiple aspects and embodiments of the invention. The patent application specifically contemplates all combinations and permutations of the aspects and embodiments.

IV. Kits for Use in Medical Applications

Another aspect of the invention provides a kit for intravenous administration of an ABDNAZ formulation to a patient suffering from cancer in order to treat the cancer. The kit comprises: (i) a formulation comprising ABDNAZ, and (ii) instructions for intravenous administration of an ABDNAZ formulation to a patient suffering from cancer in order to treat the cancer according to procedures described herein.

Still another aspect of the invention provides a kit for rapid intravenous administration of an ABDNAZ formulation to a patient while minimizing injection site pain experienced by the patient. The kit comprises: (i) a formulation comprising ABDNAZ, and (ii) instructions for rapid intravenous administration of an ABDNAZ formulation to a patient while minimizing injection site pain experienced by the patient according to procedures described herein.

V. Definitions

To facilitate an understanding of the present invention, a number of terms and phrases are defined below.

The terms "a" and "an" as used herein mean "one or more" and include the plural unless the context is inappropriate.

As used herein, the term "patient" refers to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "alleviate" and "alleviating" refer to reducing the severity of the condition, such as reducing the severity by, for example, at least 10%, 20%, 30%, 40%, 50%, 60%, 70%, 80%, 90%, or 95%.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, for example, Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "about" as used herein when referring to a measurable value (e.g., weight, time, and dose) is meant to encompass variations, such as ±10%, ±5%, ±1%, or ±0.1% of the specified value.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

EXAMPLES

The invention now being generally described, will be more readily understood by reference to the following examples, which are included merely for purposes of illustration of certain aspects and embodiments of the present invention, and are not intended to limit the invention.

Example 1—Intravenous Administration of an ABDNAZ Formulation Formed by Combining Whole Blood, Abdnaz, and an Anticoagulant As part of a clinical trial, twelve, adult human patients were intravenously administered an ABDNAZ formulation formed by combining whole blood, ABDNAZ (4 mg), an anticoagulant, and certain other materials as described in more detail below. Intravenous administration of the ABDNAZ formulation was performed at an initial flow rate of 5 mL/minute. The procedure permitted an increase in the flow rate if tolerable to the patient. No patients reported experiencing pain at the injection site. Further description of experimental procedures and results are provided below.

Part I—Experimental Procedures

As part of a clinical trial, twelve, adult human patients were intravenously administered an ABDNAZ formulation. The intravenous administration was central venous administration. The ABDNAZ formulation was prepared as follows:

(1) Approximately 100 mL of the patient's blood as drawn and then combined with an 11 mL aliquot of ACD-A solution (which is an anticoagulant solution containing sodium citrate, such as that commercially available from Citra Labs) to produce Solution No. 1;

(2) Solution No. 1 was mixed with 4 mL of a solution containing ABDNAZ (4 mg), polyethylene glycol having a number average molecular weight of 400 g/mol (6% w/w), dimethylacetamide (3% w/w), and water for injection, to produce the ABDNAZ formulation.

The ABDNAZ formulation was passed through a sterile filter and intravenously administered to the patient at an initial flow rate of 5 mL/minute. The flow rate could be increased if tolerable to the patient. At an infusion rate of 5 mL/minute, the ABDNAZ formulation having a volume of 115 mL can be intravenously administered in about 23 minutes.

Part II—Results

No patients reported experiencing pain at the injection site.

Example 2—Intravenous Administration of an ABDNAZ Formulation Containing ABDNAZ, Peg-400, Dimethylacetamide, and Water An aqueous solution of ABDNAZ was intravenously administered to twenty-five human patients as part of a Phase I clinical study. The aqueous solution contained ABDNAZ (2 mg/mL), polyethylene glycol having a number average molecular weight of 400 g/mol (6% w/w), dimethylacetamide (3% w/w), and water for injection. Patients were administered a volume of the aqueous solution of ABDNAZ sufficient to deliver a dose of ABDNAZ in the amount of 10 mg/m$^2$, 16.7 mg/m$^2$, 24.6 mg/m$^2$, 33 mg/m$^2$, 55 mg/m$^2$, or 83 mg/m$^2$. Pain at the injection site due to administration of the aqueous solution of ABDNAZ was experienced by 84% of patients. The first patient to receive the aqueous solution of ABDNAZ by central intravenous administration over a period of 20 minutes to deliver a 10 mg/m$^2$ dose of ABDNAZ experienced infusion-site pain and nasopharyngeal burning sensation of such high intensity that the patient voluntarily withdrew from the study. Thereafter, peripheral intravenous delivery in the antecubital or forearm area was used and a longer duration of time was used to perform the infusion (e.g., ranging from 2 hours to 8 hours, while administering at a rate of 3.5 mL/hour that could be adjusted up or down in 0.5 mL/hour increments based on patients' ability to tolerate the infusion). Further description of experimental procedures and results are provided below.

Part I—Experimental Procedures

In this open-label, human, dose-escalation phase 1 study, a 3+3 dose-escalation design was used to assess safety, tolerability, and pharmacokinetics of ABDNAZ. Patients were enrolled from the University of California—San Diego Moores Cancer Center, La Jolla, Calif., USA, and the Sarah Cannon Research Institute, Nashville, Tenn., USA. Eligible patients were 18 years or older with histologically confirmed advanced solid tumours for which standard curative treatment did not exist. All patients had an Eastern Cooperative Group performance status of 2 or less, an estimated life expectancy of at least 12 weeks, and adequate laboratory parameters (absolute neutrophil count ≥1.5×10$^6$ cells per L, platelet count ≥7.5×10$^6$ cells per L, haemoglobin ≥90 g/L, serum total bilirubin ≤427.5 μmol/L, aspartate amino transferase and alanine aminotransferase concentration ≤2.5 times the upper normal limit [ULN; <5 times the ULN for hepatic involvement], and creatinine clearance >50 mL per min). Previous antineoplastic therapies had to have been discontinued at least 6 weeks before intervention start, and patients could show no residual side-effects of previous therapies. Patients were required to practice effective contraception while receiving ABDNAZ. All patients had evaluable disease. Key exclusion criteria included hypoalbuminaemia (albumin <30 g/L), active brain metastases (although patients with stable brain metastases were eligible), pregnancy or breast feeding, any other clinically significant illness or psychiatric disorder that could affect compliance or endpoint assessments, and concurrent use of any other investigational drugs.

Screening assessments were done at the clinical site less than 16 days before treatment initiation and included an electrocardiogram, urinalysis, Modified Borg Dyspnea Assessment, pulse oximetry, and radiographic tumour measurement. A medical history, physical examination, pregnancy test, performance status, complete blood count, a comprehensive serum chemistry, and urinalysis were done within 16 days of the first dosing.

The protocol was reviewed and approved by the investigational review boards at the Moores Cancer Center and the Sarah Cannon Research Institute. All procedures were performed in accordance with the principles established by the Helsinki Declaration. Patients gave written informed consent for all clinical and research aspects of the study before enrolment, which was done according to national and institutional guidelines.

An aqueous solution of ABDNAZ was intravenously administered to patients. The aqueous solution contained ABDNAZ (2 mg/mL), polyethylene glycol having a number average molecular weight of 400 g/mol (6% w/w), dimethylacetamide (3% w/w), and water for injection. Patients were administered a volume of the aqueous solution of ABDNAZ sufficient to deliver a dose of ABDNAZ in the amount of 10 mg/m$^2$, 16.7 mg/m$^2$, 24.6 mg/m$^2$, 33 mg/m$^2$, 55 mg/m$^2$, or 83 mg/m$^2$. Three patients were given a starting dose of 10 mg/m$^2$ of ABDNAZ before dose escalation (to 16.7 mg/m$^2$, 24.6 mg/m$^2$, 33 mg/m$^2$, 55 mg/m$^2$, and 83 mg/m$^2$), with at least three patients per dose cohort, allowing a 2-week observation period before dose escalation. The duration of infusion was titrated to patient tolerance and varied between dose cohorts and patients. However, for the first patient in the 10 mg/m$^2$ dose cohort, the aqueous solution of ABDNAZ was administered centrally over 20 min, and the patient experienced infusion-site pain and nasopharyngeal burning sensation of such high intensity that the patient voluntarily withdrew from the study. Thereafter, peripheral intravenous delivery in the antecubital or forearm area was used and a longer duration of time was used to perform the infusion (e.g., ranging from 2 hours to 8 hours, while administering at a rate of 3.5 mL/hour that could be adjusted up or down in 0.5 mL/hour increments based on patients' ability to tolerate the infusion). The peripheral intravenous delivery was better tolerated; most patients showed a prominent dose-dependent vasodilation in the forearm and transient mild-to-moderate pain. For some patients in the highest dose cohort (83 mg/m$^2$), we had to split the total dose and delivery of ABDNAZ into a twice-weekly regimen. Three patients in the highest dose cohort and one patient in the penultimate dose cohort (55 mg/m$^2$) needed a dose reduction to 33 mg/m$^2$ because of localized infusion pain.

Part II—Results

Pain at the injection site, mostly grade 1 and grade 2, was the most common adverse event related to treatment, experienced by 21 (84%) patients. Other common ABDNAZ-related adverse events included arm swelling or oedema (eight [32%] patients), and vein hardening (seven [28%] patients). Time constraints related to management of infusion pain from ABDNAZ resulted in a maximally feasible dose of 83 mg/m$^2$. ABDNAZ-related adverse events observed during the study are listed in the table below.

considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method for intravenous administration of an ABDNAZ formulation to a patient suffering from cancer in order to treat the cancer, the method comprising intravenously administering to the patient in need thereof a therapeutically effective amount of an ABDNAZ formulation comprising at least 60% v/v of whole blood, 10 μg/mL to 1 mg/mL of 2-bromo-1-(3,3-dinitroazetidin-1-yl)ethanone ("ABDNAZ"), and an anticoagulant, in order to treat the cancer.

2. The method of claim 1, wherein the whole blood is autologous whole blood.

3. The method of claim 1, wherein the ABDNAZ formulation is intravenously administered to the patient at a rate of at least 30 mL/hour.

4. The method of claim 1, wherein the ABDNAZ formulation is intravenously administered to the patient at a rate of at least 60 mL/hour.

5. The method of claim 1, wherein the cancer is a solid tumor.

6. The method of claim 1, wherein the cancer is brain cancer, bladder cancer, breast cancer, cervical cancer, cholangiocarcinoma, colon cancer, colorectal cancer, endometrial cancer, esophageal cancer, lung cancer, liver cancer, melanoma, ovarian cancer, pancreatic cancer, prostate cancer, rectal cancer, renal cancer, stomach cancer, testicular cancer, or uterine cancer.

7. The method of claim 1, wherein the cancer is a leukemia or lymphoma.

8. The method of claim 1, wherein the ABDNAZ formulation consists of whole blood, ABDNAZ, an anticoagulant, and optionally one or more of water, a polyethylene glycol, and N,N-dimethylacetamide.

9. The method of claim 1, wherein intravenous administration of the ABDNAZ formulation commences within about 1 hour after formation of the ABDNAZ formulation.

|  | 10 mg/m$^2$ Dose ABDNAZ (n = 6) | | 16.7 mg/m$^2$ Dose ABDNAZ (n = 3) | | 24.6 mg/m$^2$ Dose ABDNAZ (n = 3) | | 33 mg/m$^2$ Dose ABDNAZ (n = 4) | | 55 mg/m$^2$ Dose ABDNAZ (n = 3) | | 83 mg/m$^2$ Dose ABDNAZ (n = 6) | |
|---|---|---|---|---|---|---|---|---|---|---|---|---|
| Adverse Event | Grade 1-2 | Grade 3 | Grade 1-2 | Grade 3 | Grade 1-2 | Grade 3 | Grade 1-2 | Grade 3 | Grade 1-2 | Grade 3 | Grade 1-2 | Grade 3 |
| Infusion-site pain | 4 (67%) | 0 | 3 (100%) | 0 | 1 (33%) | 0 | 3 (75%) | 1 (25%) | 3 (100%) | 0 | 6 (100%) | 0 |
| Arm swelling or oedema | 0 | 0 | 1 (33%) | 0 | 0 | 0 | 1 (25%) | 0 | 2 (67%) | 0 | 4 (67%) | 0 |
| Vein hardening | 0 | 0 | 0 | 0 | 0 | 0 | 1 (25%) | 0 | 1 (33%) | 0 | 5 (83%) | 0 |
| Dyspnoea or wheezing | 1 (17%) | 0 | 0 | 0 | 0 | 0 | 0 | 0 | 1 (33%) | 0 | 3 (50%) | 0 |
| Mouth tingling or burning | 0 | 0 | 0 | 0 | 0 | 0 | 0 | 0 | 2 (67%) | 0 | 2 (33%) | 0 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be 10. The method of claim 1, further comprising obtaining an aliquot of whole blood from the patient, and then using said aliquot to prepare the ABDNAZ formulation for administration to the patient.

11. The method of claim 1, wherein the patient has at least 95% of the amount of their average daily blood volume.

12. The method of claim 11, wherein the whole blood is autologous whole blood.

13. The method of claim 11, wherein the ABDNAZ formulation is intravenously administered to the patient at a rate of at least 30 mL/hour.

14. The method of claim 11, wherein the ABDNAZ formulation is intravenously administered to the patient at a rate of at least 60 mL/hour.

15. The method of claim 11, wherein the cancer is a solid tumor.

16. The method of claim 11, wherein the cancer is brain cancer, bladder cancer, breast cancer, cervical cancer, cholangiocarcinoma, colon cancer, colorectal cancer, endometrial cancer, esophageal cancer, lung cancer, liver cancer, melanoma, ovarian cancer, pancreatic cancer, prostate cancer, rectal cancer, renal cancer, stomach cancer, testicular cancer, or uterine cancer.

17. The method of claim 11, wherein the cancer is a leukemia or lymphoma.

18. The method of claim 11, wherein the ABDNAZ formulation consists of whole blood, ABDNAZ, an anticoagulant, and optionally one or more of water, a polyethylene glycol, and N,N-dimethylacetamide.

19. The method of claim 1, wherein any pain experienced by the patient at the site of intravenous administration of the ABDNAZ formulation due to intravenous administration of the ABDNAZ formulation is no greater than Grade 2.

* * * * *